(12) United States Patent
Overstreet et al.

(10) Patent No.: US 7,616,999 B2
(45) Date of Patent: *Nov. 10, 2009

(54) SYSTEM FOR GENERATING A COCHLEAR IMPLANT PROGRAM USING MULTI-ELECTRODE STIMULATION TO ELICIT THE ELECTRICALLY-EVOKED COMPOUND ACTION POTENTIAL

(75) Inventors: Edward H Overstreet, Valencia, CA (US); Leonid M Litvak, Los Angeles, CA (US); Michael A Faltys, Northridge, CA (US)

(73) Assignee: Advanced Bionics, LLC, Valencia, CA (US)

( * ) Notice: Subject to any disclaimer, the term of this patent is extended or adjusted under 35 U.S.C. 154(b) by 269 days.

This patent is subject to a terminal disclaimer.

(21) Appl. No.: 11/697,605

(22) Filed: Apr. 6, 2007

(65) Prior Publication Data

US 2007/0179565 A1    Aug. 2, 2007

Related U.S. Application Data

(63) Continuation of application No. 10/698,098, filed on Oct. 31, 2003, now Pat. No. 7,206,640.

(60) Provisional application No. 60/425,208, filed on Nov. 8, 2002.

(51) Int. Cl.
*A61N 1/18* (2006.01)

(52) U.S. Cl. .......................................... 607/56; 607/57
(58) Field of Classification Search .............. 607/55–57
See application file for complete search history.

(56) References Cited

U.S. PATENT DOCUMENTS

| | | | | |
|---|---|---|---|---|
| 6,175,767 | B1 * | 1/2001 | Doyle, Sr. ..................... | 607/57 |
| 6,205,360 | B1 * | 3/2001 | Carter et al. .................. | 607/57 |
| 6,915,166 | B1 * | 7/2005 | Stecker et al. ................. | 607/55 |
| 7,206,640 | B1 * | 4/2007 | Overstreet .................... | 607/57 |

* cited by examiner

*Primary Examiner*—Carl H Layno
*Assistant Examiner*—Brian T Gedeon
(74) *Attorney, Agent, or Firm*—AdvantEdge Law Group, LLC

(57) ABSTRACT

A multichannel cochlear implant system spatially spreads the excitation pattern in the target neural tissue by either: (1) rapid sequential stimulation of a small group of electrodes, or (2) simultaneously stimulating a small group of electrodes. Such multi-electrode stimulation stimulates a greater number of neurons in a synchronous manner, thereby increasing the amplitude of the extra-cellular voltage fluctuation and facilitating its recording. The electrical stimuli are applied simultaneously (or sequentially at a rapid rate) on selected small groups of electrodes while monitoring the evoked compound action potential (ECAP) on a nearby electrode. The presence of an observable ECAP not only validates operation of the implant device at a time when the patient may be unconscious or otherwise unable to provide subjective feedback, but also provides a way for the magnitude of the observed ECAP to be recorded as a function of the amplitude of the applied stimulus. From this data, a safe, efficacious and comfortable threshold level can be obtained which may be used thereafter as the initial setting of the stimulation parameters of the neurostimulation device, or to guide the setting of the stimulation parameters of the neurostimulation device.

6 Claims, 13 Drawing Sheets

FIG. 6E

SYSTEM FOR GENERATING A COCHLEAR IMPLANT PROGRAM USING MULTI-ELECTRODE STIMULATION TO ELICIT THE ELECTRICALLY-EVOKED COMPOUND ACTION POTENTIAL

The present application is a Continuation of U.S. patent application Ser. No. 10/698,098, filed Oct. 31, 2003, which claims the benefit of U.S. Provisional Patent Application Ser. No. 60/425,208, filed Nov. 08, 2002.

BACKGROUND OF THE INVENTION

The present disclosure relates to neurostimulator implant devices, and more particularly to a system and method that uses multi-electrode stimulation provided by a neurostimulator implant device to elicit electrically-evoked compound action potentials. Such an evoked compound action potential (ECAP) provides valuable objective feedback information useful in setting the stimulation parameters associated with the neurostimulator implant device.

Traditional methods used to elicit the electrically-evoked compound action potential, or ECAP, deliver stimulation to a single electrode contact. There are cases where such application of a stimulus to a single electrode contact do not evoke a suitable action potential. The present disclosure provides an improved system and method for obtaining the ECAP through application of the stimulus to multiple electrodes. The present disclosure may be used in many different kinds of neurostimulator devices, but will be described in terms of a cochlear implant device.

Electrical stimulation of predetermined locations within the cochlea of the human ear through an intra-cochlear electrode array is described, e.g., in U.S. Pat. No. 4,400,590. The electrode array shown in the '590 patent comprises a plurality of exposed electrode pairs spaced along and imbedded in a resilient curved base for implantation in accordance with a method of surgical implantation, e.g., as described in U.S. Pat. No. 3,751,615. The system described in the '590 patent receives audio signals, i.e., sound waves, at a signal processor (or speech processor) located outside the body of a hearing impaired patient. The speech processor converts the received audio signals into modulated RF data signals that are transmitted by a cable connection through the patient's skin to an implanted multi-channel intracochlear electrode array. The modulated RF signals are demodulated into analog signals and are applied to selected ones of the plurality of exposed electrode pairs in the intra-cochlear electrode so as to electrically stimulate predetermined locations of the auditory nerve within the cochlea.

U.S. Pat. No. 5,938,691, incorporated herein by reference, shows an improved multi-channel cochlear stimulation system employing an implanted cochlear stimulator (ICS) and an externally wearable speech processor (SP). The speech processor employs a headpiece that is placed adjacent to the ear of the patient, which receives audio signals and transmits the audio signals back to the speech processor. The speech processor receives and processes the audio signals and generates data indicative of the audio signals for transcutaneous transmission to the implantable cochlear stimulator. The implantable cochlear stimulator receives the transmission from the speech processor and applies stimulation signals to a plurality of cochlea stimulating channels, each having a pair of electrodes in an electrode array associated therewith. Each of the cochlea stimulating channels uses a capacitor to couple the electrodes of the electrode array.

Other improved features of a cochlear implant system are taught, e.g., in U.S. Pat. Nos. 5,626,629; 6,067,474; 6,157,861; 6,195,585; 6,205,360; 6,219,580; 6,249,704; 6,289,247; 6,295,467; and 6,415,185;, each of which patents is also incorporated herein by reference.

The implantable cochlear stimulators described in the '629, '474, '861 and '580 patents are also able to selectively control the pulse width of stimulating pulses that are applied through the electrode array to the cochlea, and the frequency at which the stimulating pulses are applied.

One of the problems encountered when using a cochlear implant device, or many other type of neurostimulator devices, is "fitting" the device to a particular patient. Fitting involves setting the stimulation parameters, e.g., the amplitude, pulse width and frequency of the stimulation pulses to a level that is efficacious and comfortable for that patient. In the past, such "fitting" has been a very subjective process, requiring constant feedback from the patient. Some patients, however, e.g., old patients and extremely young patients, are not able to provide meaningful subjective feedback. Hence, clinicians are constantly looking for improved ways to obtain objective feedback from the patient that can assist in setting the stimulation parameters.

One type of objective feedback that has been used in the past is to monitor the stapedius reflex. The implantable cochlear stimulators described in the '861 and '585 patents teach the use of the stapedius reflex (also referred to as the stapedial reflex) as a parameter for monitoring and adjusting the magnitude of the stimuli applied through the electrode array. Applicant's co-pending patent application, Ser. No. 60/412,533, filed Sep.20, 2002, incorporated herein by reference, teaches an improved way for using multi-band stimuli to obtain the Stapedial Reflex.

The new generation of cochlear implants that have the enhanced processing power, and which can provide multiple platforms for delivering electrical stimuli to the auditory nerve, including high frequency pulsitile stimulation having current pulses of controlled amplitude, width and frequency, have sometimes been referred to as a "bionic ear" implant.

As the art of cochlear stimulation has advanced to produce bionic ear implants, the implanted portion of the cochlear stimulation system, and the externally wearable processor (or speech processor) have become increasingly complicated and sophisticated. It is also noted that much of the circuitry previously employed in the externally wearable processor has been moved to the implanted portion, thereby reducing the amount of information that must be transmitted from the external wearable processor to the implanted portion. The amount of control and discretion exercisable by an audiologist in selecting the modes and methods of operation of the cochlear stimulation system have increased dramatically and it is no longer possible to fully control and customize the operation of the cochlear stimulation system through the use of, for example, switches located on the speech processor. As a result, it has become necessary to utilize an implantable cochlear stimulator fitting system to establish the operating modes and methods of the cochlear stimulation system and then to download such programming into the speech processor. One such fitting system is described in the '629 patent. Another fitting system is described in the '247 patent.

The '247 patent further highlights representative stimulation strategies that may be employed by a multichannel stimulation system. Such strategies represent the manner or technique in which the stimulation current is applied to the electrodes of an electrode array used with the stimulation system. Such stimulation strategies, all of which apply current pulses to selected electrodes, may be broadly classified as: (1) sequential or non-simultaneous (where only one electrode receives a current pulse at the same time); (2) simultaneous (where substantially all of the electrodes receive current stimuli at the same time, thereby approximating an analog signal); or (3) partially simultaneous pulsitile stimulation (where only a select grouping of the electrodes receive stimuli at the same time in accordance with a predefined pattern).

Typically, when the fitting systems described in the '629 or '247 patents are employed for multichannel stimulation systems, or when equivalent or similar fitting systems are employed, it is necessary to use directly measured threshold values and/or thresholds derived from the measurement of psycophysically-determined pseudo-comfort levels. That is, for each channel of the multichannel system, a minimum threshold level is measured, typically referred to as a "T" level, which represents the minimum stimulation current which when applied to a given electrode associated with the channel produces a sensed perception of sound at least 50% of the time. In a similar manner, an "M" level is determined for each channel, which represents a stimulation current which when applied to the given electrode produces a sensed perception of sound that is moderately loud, or comfortably loud, but not so loud that the perceived sound is uncomfortable. These "T" and "M" levels are then used by the fitting software in order to properly map sensed sound to stimulation current levels that can be perceived by the patient as sound.

Disadvantageously, determining the "T" and/or "M" levels (or other required thresholds) associated with each channel of a multichannel stimulation system is an extremely painstaking and time-intensive task. Such determinations require significant time commitments on the part of the clinician, as well as the patient. Moreover, once determined one channel at a time, such levels may not be representative of actual threshold levels that are present during real speech. That is, preliminary data indicate that thresholds set in single channel psychophysics overestimate the actual threshold required when all channels are running during live speech. Such an overestimation appears to penalize patient performance, particularly performance in noise. Hence, neural stimulation parameters which render threshold measurement unnecessary would dramatically reduce the time requirements for programming sequential and/or partially simultaneous pulsitile stimulation, as well as facilitate a higher probability of optimized programming for pediatric as well as adult populations where obtaining such measures are difficult.

As the ages of patients into which implantable cochlear stimulators are implanted decreases, it becomes increasingly more important to improve the fitting process and to minimize, or eliminate, the need to make threshold measurements. This is because very young patients, for example, two year olds, are unable to provide adequate subjective feedback to the audiologist for the audiologist to accurately "fit" the cochlear stimulation system optimally for the patient. Thus, what is needed is an improved apparatus and simplified method for fitting a speech processor where many of the threshold measurements previously required are no longer needed, or where subjective feedback from the patient is no longer needed.

As indicated, one technique that has been investigated for improving the manner in which threshold measurements are made or used is to sense the stapedius reflex of the patient in response to an applied stimulus. See, e.g., the '861 and '585 patents, previously incorporated herein by reference. An electrode that may be used to sense the stapedius reflex is described, e.g., in U.S. Pat. No. 6,208,882, also incorporated herein by reference.

When the stapedius reflex is sensed, i.e., when a stapedius reflex electrode is in place that allows the stapedius reflex to be sensed, or when other techniques are used to sense the stapedius reflex, such sensing eliminates or minimizes the need to rely solely upon subjective feedback from the patient during the fitting or adjusting process. Such subjective feedback can be highly unreliable, particularly in younger and older patients.

Traditional methods for measuring stapedial reflexes present stimuli, typically pulse trains, on a single electrode and the reflex is either directly observed by visual inspection or is inferred from a change in the impedance of the tympanic membrane.

Another technique that has been investigated for improving the manner in which threshold measurements are made is to measure an evoked compound action potential (ECAP). Such ECAP measurement is particularly useful at or near the time of implant when the patient may be under the influence of anesthesia (and therefore unavailable for subjective feedback), and at a time when it is desirable for the surgeon and other clinicians associated with the implant operation to know if the implant device is working properly. An ECAP measurement is typically made by applying a stimulus to one electrode contact while monitoring the evoked action potential on an adjacent electrode contact. That is, one electrode contact is used to apply the stimulus, and an adjacent electrode contact is used as a sensor to sense the action potential (a voltage waveform) evoked by the application of the stimulus. Advantageously, in order to make an ECAP measurement, no additional electrodes or equipment are needed, beyond the neurostimulator itself, and a means of monitoring the voltage appearing on a selected electrode contact in response to application of a stimulus on a nearby electrode contact.

Disadvantageously, there are cases where it is difficult to obtain neural response measurements, e.g., an ECAP, on a given patient. In some instances, the maximal level of comfort of the patient is reached prior to seeing the ECAP, and in others the compliance level of the neurostimulator system is reached before ECAP visualization. That is, the delivery of a stimulus pulse on a single electrode contact may fail to synchronize enough neural fibers to produce a measurable evoked response. Alternatively, the delivery of a stimulus pulse on a single electrode having sufficient amplitude to evoke an action potential may exceed the compliance limits of the neurostimulator device on a single contact.

It is thus seen that improvements are still needed in the manner in which an ECAP is obtained and used during the fitting and operation of a neurostimulator implant device, e.g., a cochlear implant system.

SUMMARY OF THE INVENTION

The present specification addresses the above and other needs by spatially spreading the excitation pattern in the cochlea (or other target neural tissue) by either: (1) rapid sequential stimulation of a small group of electrodes, or (2) simultaneously stimulating a small group of electrodes. Such multi-electrode stimulation advantageously stimulates a greater number of neurons in a synchronous manner, thereby increasing the amplitude of the extra-cellular voltage fluctuation and facilitating its recording.

The present specification is intended for use with multichannel neurostimulation systems, e.g., multichannel cochlear stimulation systems, wherein stimuli can be applied simultaneously to multiple channels, or can be applied sequentially to multiple channels at a sufficiently fast rate so as to provide a synchronous response.

For example, electrical stimuli are applied simultaneously (or sequentially at a rapid rate) on selected small groups of electrodes while monitoring the ECAP on a nearby electrode. The presence of an observable ECAP advantageously validates operation of the implant device at a time when the patient may be unconscious or otherwise unable to provide subjective feedback.

In another example, the magnitude of the observed ECAP is recorded (or otherwise observed, or saved) as a function of the amplitude of the applied stimulus. From this data, an appropriate (safe, efficacious and comfortable) threshold level can be obtained which may be used as the initial setting of the stimulation parameters of the neurostimulation device, or which may be used to guide or steer the setting of the stimulation parameters of the neurostimulation device.

In another example, stimulus levels are progressively set in bands, e.g., groups of electrodes or channels. By progressively setting threshold levels in bands, either overlapping or non-overlapping, a set of data is obtained (which set of data may be smoothed, as required, using, e.g., a 3-point weighted average, b-spleen interpolation, or other known smoothing techniques) that provides a basis for setting appropriate (safe, efficacious and comfortable) stimulation parameters for each individual electrode contact during operation of the neurostimulator device.

Thus, the present specification describes an improved system and method of fitting a neurostimulator device by measuring the ECAP of the patient through application of multiband (i.e., multi-electrode contact) stimulation in order to better determine appropriate intensity threshold levels used by the implant system during its operation.

The present specification further describes such an improved system and method of fitting that does not require subjective feedback from the patient during the fitting procedure.

The present specification further describes such an improved technique for evoking a compound action potential for the purpose of validating proper operation of the implant device at a time shortly after the device is implanted at a time when the patient may still be under the influence of an anesthesia, and hence unconscious.

BRIEF DESCRIPTION OF THE DRAWINGS

The above and other aspects, features and advantages of the present invention will be more apparent from the following more particular description thereof, presented in conjunction with the following drawings wherein:

FIGS. 6A-6G illustrate representative screens that are displayed during a fitting process, such as the process shown in FIG. 5, and further illustrate a preferred algorithm used to process the measured ECAP values so as to provide initial threshold values that may be used during operation of the implant device.

Corresponding reference characters indicate corresponding components throughout the several views of the drawings.

DETAILED DESCRIPTION OF THE INVENTION

The following description is of the best mode presently contemplated for carrying out the invention. This description is not to be taken in a limiting sense, but is made merely for the purpose of describing the general principles of the invention. The scope of the invention should be determined with reference to the claims.

Figure 1:
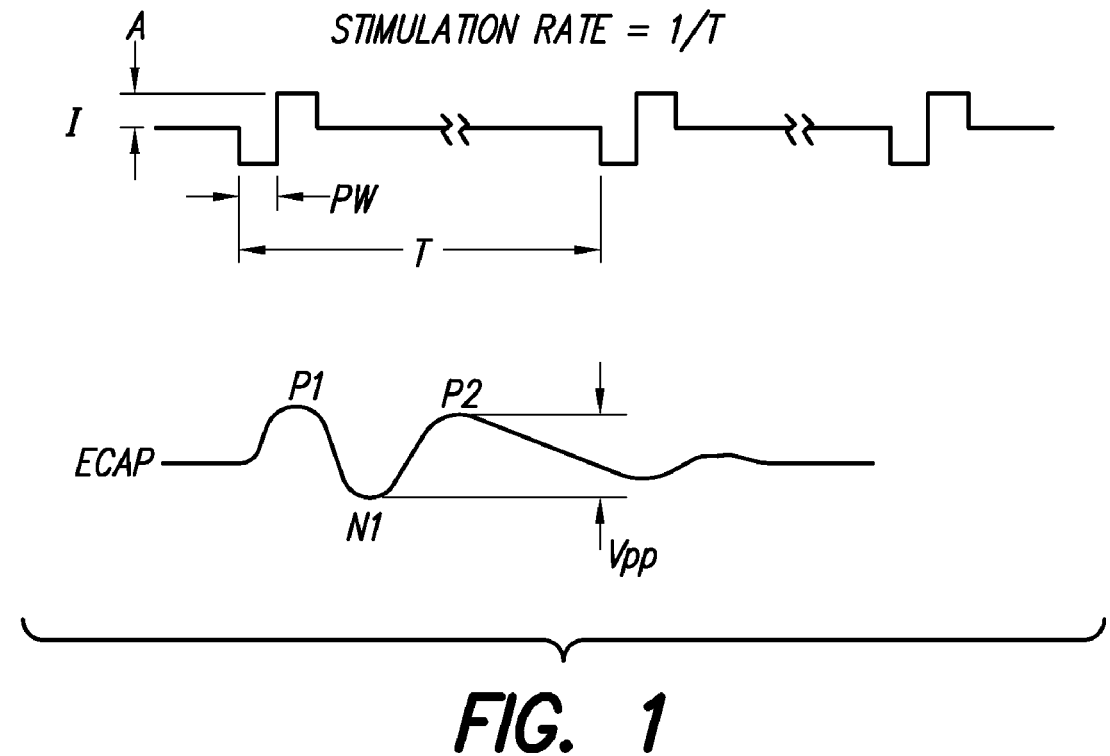
FIG. 1 shows a current stimulation waveform and a corresponding evoked compound action potential (ECAP), and defines the stimulation rate (1/T), amplitude (A) and biphasic pulse width (PW) associated with the electrical stimuli, and the peak-to-peak amplitude ($V_{pp}$) and general waveform shape typically associated with the ECAP.

FIG. 1 shows a current stimulation waveform (I) and a corresponding evoked compound action potential (ECAP). FIG. 1 defines the stimulation rate (1/T), amplitude (A) and biphasic pulse width (PW) associated with the current stimulation waveform FIG. 1 also illustrates a typical ECAP waveform that is evoked in response to the applied current stimulation waveform. Such ECAP waveform is typically characterized by three humps, or peaks, labeled P1, N1,and P2. The first peak P1 is, as illustrated in FIG. 1, a positive peak and is often difficult to measure, as it may be swamped out by other electrical activity. The second peak N1, as illustrated in FIG. 1, is a negative peak. The third peak P2, as illustrated in FIG. 1, is another positive peak. While numerous parameters associated with the ECAP waveform may be monitored or measured, a preferred parameter is the peak-to-peak amplitude between the peaks N1 and P2, labeled VPP in FIG. 1. It should be noted that in some instances, depending upon the polarity of the leads used to monitor the ECAP waveform, the waveform shown in FIG. 1 may be inverted, i.e., with P1 and P2 being negative peaks, and N1 being a positive peak. Such inversion does not significantly alter the peak-to-peak value VPP used herein as a measure of the ECAP amplitude.

Figure 2A:
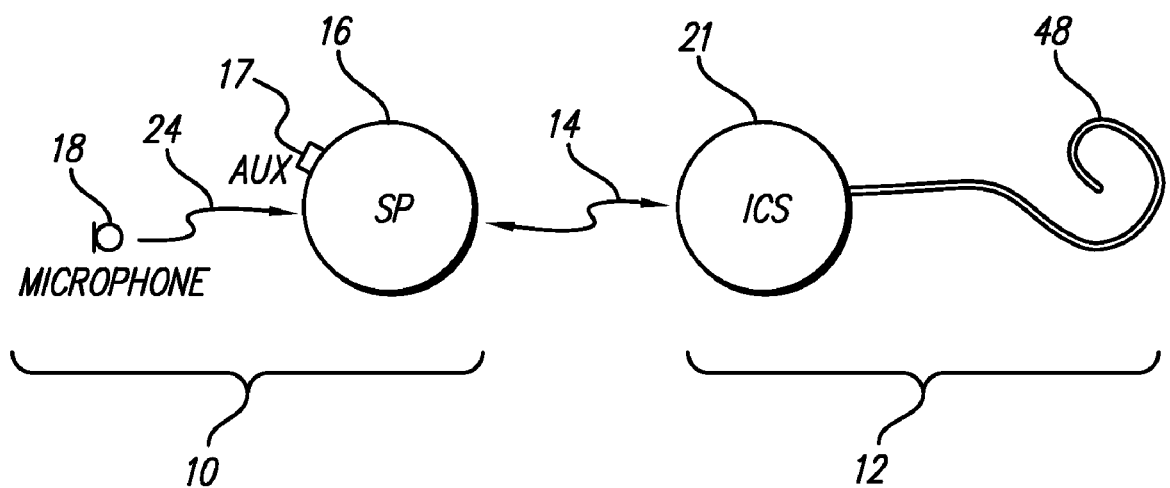
FIGS. 2A and 2B respectively show a cochlear implant system and a partial functional block diagram of the cochlear stimulation system, which system is capable of providing high rate pulsitile electrical stimuli on multiple channels.

FIG. 2A shows a representative neurostimulation system, i.e., a cochlear stimulation system. The principles described herein will be described in terms of a cochlear stimulation system. However, it is to be understood that these principles may be used with any type of multichannel neurostimulation system.

The cochlear stimulation system shown in FIG. 2A includes a speech processor portion 10 and a cochlear stimulation portion 12. The speech processor portion 10 includes a speech processor (SP) 16 and a microphone 18. The microphone 18 may be connected directly to the SP 16, or may be coupled to the SP 16 through an appropriate communication link 24. An auxiliary input port 17 may also be part of the speech processor 16 to allow input signals from a source other than the microphone 18 to be input into the SP 16.

The cochlear stimulation portion 12 includes an implantable cochlear stimulator (ICS) 21 and an electrode array 48. The electrode array 48 is adapted to be inserted within the cochlea of a patient so as to be adjacent target tissue within the cochlea that is to be stimulated. The array 48 includes a multiplicity of electrodes, e.g., sixteen electrodes, spaced along its length that are selectively connected to the ICS 21. The electrode array 48 may be substantially as shown and described in U.S. Pat. Nos. 4,819,647 or 6,129,753, incorporated herein by reference. Electronic circuitry within the ICS 21 allows a specified stimulation current to be applied to selected pairs or groups of the individual electrodes included within the electrode array 48 in accordance with a specified stimulation pattern, defined by the SP 16.

The ICS 21 and the SP 16 are shown in FIG. 2A as being linked together electronically through a suitable data or communications link 14. In some cochlear implant systems, the SP 16, auxiliary input port 17 and microphone 18 comprise the external portion of the cochlear implant system; and the ICS 21 and electrode array 48 comprise the implantable portion of the system. Thus, the data link 14 is a transcutaneous data link that allows power and control signals to be sent from the SP 16 to the ICS 21. In some embodiments, data and status signals may also be sent from the ICS 21 to the SP 16. The sending of data and status signals from the ICS 21 to the SP 16 is referred to as "backtelemetry".

In modern cochlear implant systems, as shown more particularly below in FIG. 2B, at least certain portions of the SP 16 are included within the implantable portion of the overall cochlear implant system, while other portions of the SP 16 remain in the external portion of the system. In general, at least the microphone 18 (and auxiliary input port 17, if used) and associated analog front end (AFE) circuitry 22 will be part of the external portion of the system; and at least the ICS 21 and electrode array 48 are part of the implantable portion of the invention. As used herein, "external" means not implanted under the skin or residing within the inner ear. However, "external" may mean within the outer ear, including in the ear canal, and may also include within the middle ear.

Typically, where a transcutaneous data link must be established between the external portion and implantable portions of the system, such link is realized by an internal antenna coil within the implantable portion, and an external antenna coil within the external portion. In use, the external antenna coil is positioned so as to be aligned over the location where the internal antenna coil is implanted, allowing such coils to be inductively coupled to each other, thereby allowing data (e.g., the magnitude and polarity of a sensed acoustic signals) and power to be transmitted from the external portion to the implantable portion. Note, in other embodiments of the invention, both the SP 16 and the ICS 21 may be implanted within the patient, either in the same housing or in separate housings. If in the same housing, the link 14 may be realized with a direct wire connection within such housing. If in separate housings, as taught, e.g., in U.S. Pat. No. 6,067,474, incorporated herein by reference, the link 14 may be an inductive link using a coil or a wire loop coupled to the respective parts.

The microphone 18 senses acoustic signals and converts such sensed signals to corresponding electrical signals, and may thus be considered as an acoustic transducer. The electrical signals are sent to the SP 16 over a suitable electrical or other link 24. Alternatively, electrical signals may be input directly into the auxiliary input port 17 from a suitable signal source. The SP 16 processes the converted acoustic signals received from the microphone, or the electrical signals received through the auxiliary input port 17, in accordance with a selected speech processing strategy in order to generate appropriate control signals for controlling the ICS 21. In operation, such control signals specify or define the polarity, magnitude, location (which electrode pair or other group of electrodes receives the stimulation current), and timing (when the stimulation current is applied to the electrode pair or other group) of the stimulation current that is generated by the ICS. Such control signals thus combine to produce a desired spatiotemporal pattern of electrical stimuli in accordance with the desired speech processing strategy. Unlike early cochlear implant systems, more modern cochlear implant systems advantageously confine such control signals to circuitry within the implantable portion of the system, thereby avoiding the need to continually send or transmit such control signals across a transcutaneous link.

The speech processing strategy is used, inter alia, to condition the magnitude and polarity of the stimulation current applied to the implanted electrodes of the electrode array 48. Such speech processing strategy involves defining a pattern of stimulation waveforms that are to be applied to the electrodes as controlled electrical currents. As described herein, during the fitting process, a strategy is used which stimulates selected groups of the implanted electrodes either simultaneously or sequentially at a high rate. Here, "high rate" means any rate sufficiently fast so as to evoke a synchronized neural response from the neurons in the surrounding target tissue. In general, such sequential stimulation at a "high rate" has the same effect as would a simultaneous stimulation. For many patients, a rate greater than about 5 KHz would qualify as a "high rate" stimulation. During such stimulation, an adjacent electrode contact within the electrode array is monitored for the occurrence of an ECAP in response to the applied stimulation.

As indicated, the types of stimulation patterns applied to the electrode groups may be conveniently categorized as: (1) simultaneous stimulation patterns, or (2) non-simultaneous stimulation patterns. Simultaneous stimulation patterns may be "fully" simultaneous or partially simultaneous. A fully simultaneous stimulation pattern is one wherein stimulation currents, either analog or pulsitile, are applied to the electrodes of all of the available channels at the same time. A partially simultaneous stimulation pattern is one wherein stimulation currents, either analog or pulsitile, are applied to the electrodes of two or more channels, but not necessarily all of the channels, at the same time. Examples of each type of strategy are given in U.S. Pat. No. 6,289,247, incorporated herein by reference. A non-simultaneous stimulation pattern applies stimulation currents to electrodes in a sequential manner, e.g., only one electrode pair at a time. However, the rate of stimulation applied to different electrode pairs may be sufficiently fast so that the stimulation has the same affect as though it were applied to all of the selected electrode pairs simultaneously.

Analog waveforms used in analog stimulation patterns are typically reconstructed by the generation of continuous short monophasic pulses (samples). The sampling rate is selected to be fast enough to allow for proper reconstruction of the temporal details of the signal. An example of such a sampled analog stimulation pattern is a simultaneous analog sampler (SAS) strategy.

Current pulses applied in pulsitile stimulation patterns are generally biphasic pulses, as shown in FIG. 1, but may also be multiphasic pulses, applied to the electrodes of each channel. The biphasic/multiphasic pulse has a magnitude (e.g., amplitude "A" and/or duration "PW") that varies as a function of the sensed acoustic signal or other source of modulation. (A "biphasic" pulse is generally considered as two pulses: a first pulse of one polarity having a specified magnitude, followed immediately, or after a very short delay, by a second pulse of the opposite polarity having the same total charge, which charge is the product of stimulus current times duration of each pulse or phase.) For multichannel cochlear stimulators of the type described herein, it is common to apply a high rate biphasic stimulation pulse train to each of the pairs of electrodes in a selected group of electrodes in accordance with a selected strategy, and modulate the pulse amplitude of the pulse train as a function of information contained within the sensed acoustic signal, or the received auxiliary input signal.

Figure 2B:
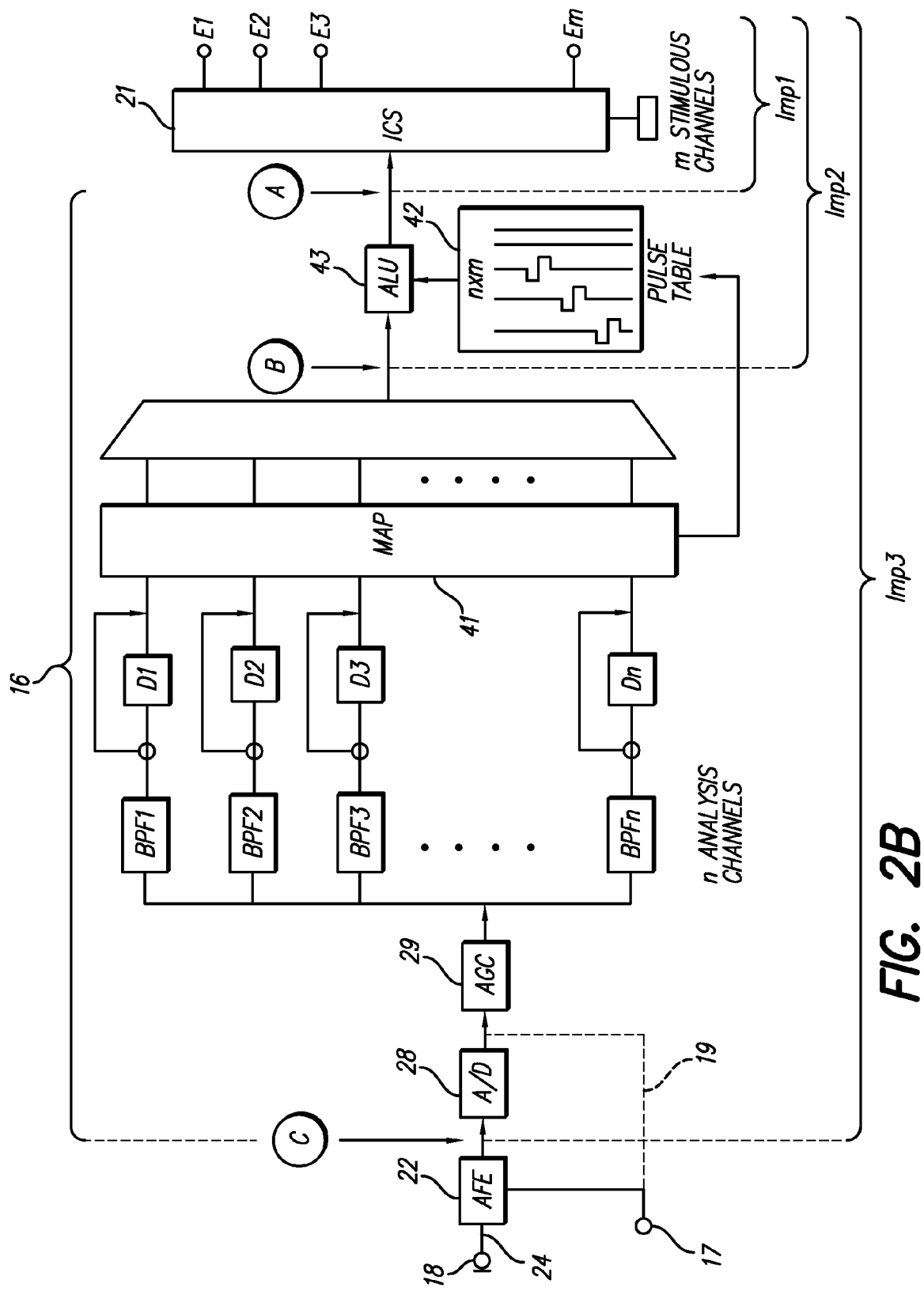

Turning next to FIG. 2B, a partial block diagram of a representative cochlear implant is shown. More particularly, FIG. 2B shows a partial functional block diagram of the SP 16 and the ICS 21 of an exemplary cochlear implant system capable of providing a high rate pulsitile stimulation pattern. That which is shown in FIG. 2B depicts the functions that are carried out by the SP 16 and the ICS 21. The actual electronic circuitry that is used to carry out these functions is not critical to understanding and practicing the present invention. It should also be pointed out that the particular functions shown in FIG. 2B are representative of just one type of signal processing strategy that may be employed (which divides the incoming signal into frequency bands, and independently processes each band). Other signal processing strategies could just as easily be used to process the incoming acoustical signal.

A complete description of the functional block diagram of the cochlear implant system shown in FIG. 2B is found in U.S. Pat. No. 6,219,580, incorporated herein by reference. It is to be emphasized that the functionality shown in FIG. 2B is only representative of one type of exemplary cochlear implant system, and is not intended to be limiting. The details associated with a given cochlear implant system are not critical to understanding and practicing the present invention.

In the manner described in the U.S. Pat. No. 6,219,580 the cochlear implant functionally shown in FIG. 2B provides n analysis channels that may be mapped to one or more stimulus channels. That is, as seen in FIG. 2B, after the incoming sound signal is received through the microphone 18 or auxiliary input port 17, and the analog front end circuitry (AFE) 22, it is digitized in an analog to digital (A/D) converter 28, and then subjected to appropriate gain control (which may include compression) in an automatic gain control (AGC) unit 29. (It should be noted that in some instances the signal input into the auxiliary input port 17 may already be digitized, in which case a signal path 19 is provided that bypasses the A/D converter 28.) After appropriate gain control, the signal is divided into n analysis channels, each of which includes a bandpass filter, BPFn, centered at a selected frequency. The signal present in each analysis channel is processed as described more fully in the U.S. Pat. No. 6,219,580 and the signals from each analysis channel are then mapped, using mapping function 41, so that an appropriate stimulus current, of a desired amplitude and timing, may be applied through a selected stimulus channel to stimulate the auditory nerve.

Thus it is seen that the system of FIG. 2B provides a multiplicity of channels, n, wherein the incoming signal is analyzed. The information contained in these n "analysis channels" is then appropriately processed, compressed and mapped in order to control the actual stimulus patterns that are applied to the patient by the ICS 21 and its associated electrode array 48. The electrode array 48 includes a multiplicity of electrode contacts, connected through appropriate conductors, to respective current generators, or pulse generators, within the ICS. Through these multiplicity of electrode contacts, a multiplicity of stimulus channels, e.g., m stimulus channels, exist through which individual electrical stimuli may be applied at m different stimulation sites within the patient's cochlea.

While it is common to use a one-to-one mapping scheme between the analysis channels and the stimulus channels, wherein n=m, and the signal analyzed in the first analysis channel is mapped to produce a stimulation current at the first stimulation channel, and so on, it is not necessary to do so. Rather, in some instances, a different mapping scheme may prove beneficial to the patient. For example, assume that n is not equal to m (n, for example, could be at least 20 or as high as 32, while m may be no greater than sixteen, e.g., 8 to 16). The signal resulting from analysis in the first analysis channel may be mapped, using appropriate mapping circuitry 41 or equivalent, to the first stimulation channel via a first map link, resulting in a first stimulation site (or first area of neural excitation). Similarly, the signal resulting from analysis in the second analysis channel of the SP may be mapped to the second stimulation channel via a second map link, resulting in a second stimulation site. Also, the signal resulting from analysis in the second analysis channel may be jointly mapped to the first and second stimulation channels via a joint map link. This joint link results in a stimulation site that is somewhere in between the first and second stimulation sites. The "in between site" is sometimes referred to as a virtual stimulation site. Advantageously, this possibility of using different mapping schemes between n SP analysis channels and m ICS stimulation channels to thereby produce a large number of virtual and other stimulation sites provides a great deal of flexibility with respect to positioning the neural excitation areas in a location that proves most beneficial to the patient.

Still with reference to FIG. 2B, it should be noted that the speech processing circuitry 16 generally includes all of the circuitry from point (C) to point (A). In some cochlear implant systems, the entire SP circuitry is housed in a speech processor that is part of the external (or non-implanted) portion of the system. That is, in such systems, only the ICS 21, and its associated electrode array, are implanted, as indicated by the bracket labeled "Imp1" (for "Implant-1"). This means that in such systems, the signal passing through the serial data stream at point (A) is also the signal that must pass through the transcutaneous communication link from the external unit to the implanted unit. Because such signal contains all of the defining control data for the selected speech processing strategy, for all m stimulation channels, it therefore has a fairly high data rate associated therewith. As a result of such high data rate, either the system operation must be slowed down, which is generally not desirable, or the bandwidth of the link must be increased, which is also not desirable because the operating power increases.

In contrast to Implant-1 systems, other cochlear implant systems, such as the CII Bionic Ear system manufactured by Advanced Bionics Corporation of Sylmar, Calif. advantageously puts at least a portion of the speech processor 16 within the implanted portion of the system. For example, a cochlear implant system may place the Pulse Table 42 and arithmetic logic unit (ALU) 43 inside of the implanted portion, as indicated by the bracket labeled "Imp2" in FIG. 2B. Such partitioning of the speech processor 16 offers the advantage of reducing the data rate that must be passed from the external portion of the system to the implanted portion. That is, the data stream that must be passed to the implanted portion Imp2 comprises the signal stream at point (B). This signal is essentially the digitized equivalent of the modulation data associated with each of the n analysis channels, and (depending upon the number of analysis channels and the sampling rate associated with each) may be significantly lower than the data rate associated with the signal that passes through point (A). Hence, improved performance without sacrificing power consumption may be obtained with a bionic ear implant.

Other cochlear implant systems under development will incorporate more and more of the speech processor 16 within the implanted portion of the system. For example, a fully implanted speech processor 16 incorporates all of the SP in the implanted portion, as indicated by the bracket labeled Imp3 in FIG. 2B. Such a fully implanted speech processor offers the advantage that the data input into the system, i.e., the data stream that passes through point (C), need only have a rate commensurate with the input signal received through the microphone 18 or the auxiliary input port 17.

With the preceding as background information relative to a typical cochlear implant system, which is representative of a neurostimulation system, the specification will now fully describe an improved method of fitting the neurostimulation system, i.e., a cochlear implant system, to a patient by applying stimuli to multiple bands of electrodes, e.g., multiple groups of electrodes, while monitoring the ECAP that such stimuli elicits. This is done for the purpose of helping to initially set program parameters, e.g., the amplitude of the stimulation current, so that when the implant device (e.g., the implantable cochlear stimulator) is first turned on, the intensity of the stimulation will be sufficiently strong so as to evoke a desired response, but not too strong so as to make the stimulation uncomfortable or painful for the patient.

Figure 3A:
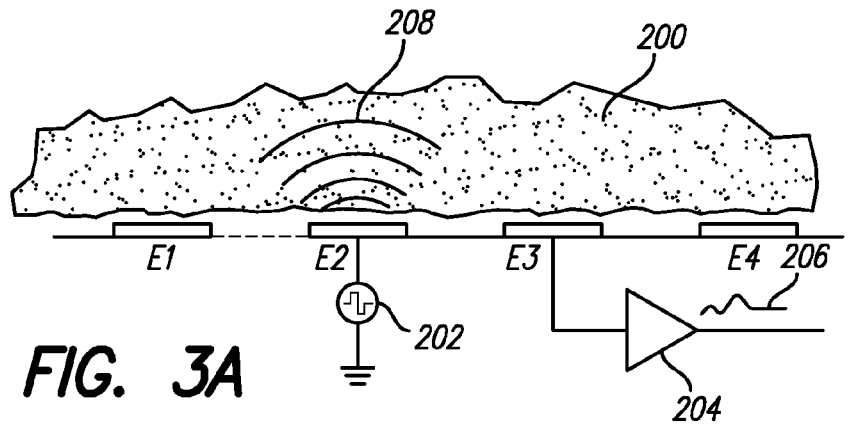
FIG. 3A conceptually illustrates the problem sometimes associated with trying to evoke a compound action potential through application of an electrical stimulus pulse on a single electrode contact.

In one example, a stimulus is applied to multiple electrode contacts either simultaneously, or sequentially at a fast rate, so as to produce a recordable ECAP. This process is conceptually illustrated in FIGS. 3A, 3B and 3C, which figures show multiple spaced-apart electrode contacts E1, E2, E3 and E4 in contact with, or near, body tissue 200 that is to be stimulated. In FIG. 3A, a stimulus current pulse is applied to electrode E2 by current source 202, while electrode E3 is used as a "sensor" to determine if the applied stimulus produces any neural response in the tissue. Such neural response would be indicated, e.g., by sensing the presence of an evoked compound action potential, or ECAP, on electrode E3. Such ECAP, if present, is sensed through sense amplifier 204 as waveform 206.

The problem with applying the current stimulus to just one electrode, as shown in FIG. 3A, is that the resulting electric field 208 that propagates out from the electrode contact E2 may not capture sufficient neural cells within its range to create the desired evoked response. Alternatively, the single current stimulus applied to just one electrode contact, e.g., electrode E2 as shown in FIG. 3A, may not have sufficient magnitude to create an electric field that propagates sufficiently far and with sufficient magnitude so as to elicit the desired ECAP response. While the amplitude of the applied stimulus can be increased until the desired ECAP is elicited, in some instances the compliance voltage of the neurostimulation device may limit the amplitude of the applied pulse to a value that is less than the value needed. The bottom line is that application of a stimulus to one electrode contact, as shown in FIG. 3A, may not always elicit the desired ECAP response.

Figure 3B:
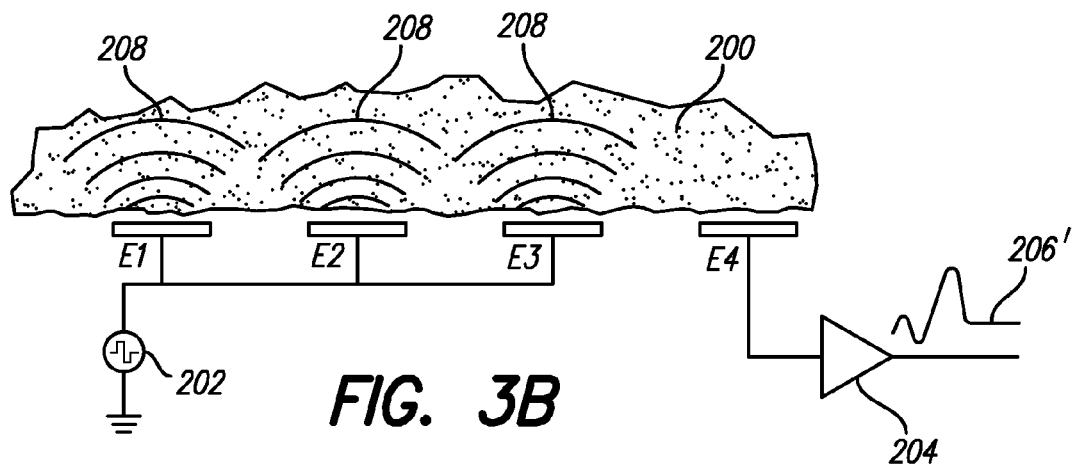
FIG. 3B conceptually illustrates simultaneous application of an electrical stimulus on multiple electrode contacts in order to evoke a compound action potential.

To overcome the limitations associated with use of a single electrode contact, as shown in FIG. 3A, the present specification describes the application of a current stimulus pulse from a current source 202 to multiple electrode contacts simultaneously, as shown in FIG. 3B. That is, as shown conceptually in FIG. 3B, the current pulse from current source 202 is applied to electrode contacts E1, E2 and E3 simultaneously, while electrode contact E4 is used as a sense electrode. The electric fields 208 that propagate into the surrounding tissue 200 from each of the electrode contacts E1, E2, and E3 affect a much larger tissue area, and are thus able to capture more neural cells, and thereby more easily produce the desired evoked response. The desired evoked response, or ECAP, is sensed through sense amplifier 204 as ECAP waveform 206'.

Figure 3C:
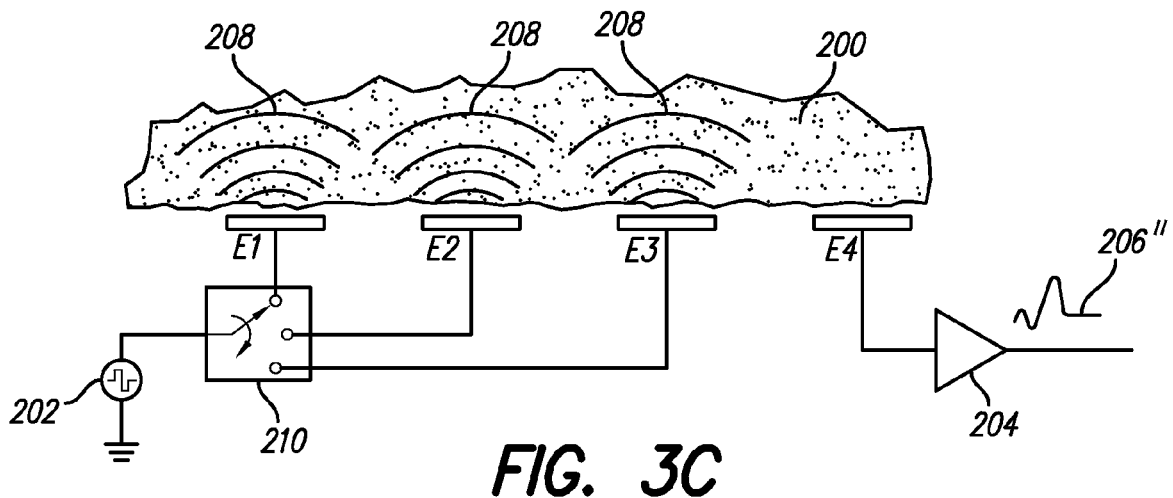
FIG. 3C conceptually illustrates rapid sequential application of an electrical stimulus on multiple electrode contacts in order to evoke a compound action potential.

As an alternative to the simultaneous approach depicted in FIG. 3B, a rapid sequential stimulation may also be used, as conceptually illustrated in FIG. 3C. As seen in FIG. 3C, a stimulus current pulse from current source 202 is applied through switch 210 in sequence to electrodes E1, E2, and E3. That is, electrode E1 first receives the pulse, followed a short time thereafter by electrode E2, and followed a short time thereafter by electrode E3. This sequencing may repeat itself, as needed. In order for the sequential approach of FIG. 3C to work it is necessary that the sequencing be done at a high (or rapid) rate. A "high rate" as previously indicated, means a rate sufficiently fast so as to produce a synchronized evoked response from the surrounding tissue. A representative high rate for stimulating cochlear tissue might be, e.g., 5 KHz or faster. Conceptually, this means that the electric field 208 that propagates out from each electrode E1, E2, E3, as each is stimulated in sequence with a stimulus pulse (which electric field has a lingering affect on the tissue 200 in which it propagates), has sufficient overlap with the adjoining electric fields so as to affect a larger tissue area, thereby capturing more neural cells, and thereby more easily producing the desired evoked response. The evoked response 206" is sensed through sense amplifier 204, which is connected to the "sense" electrode E4.

Thus it is seen that one example of the techniques described herein involves applying a stimulus pulse to multiple electrodes, either simultaneously (as represented in FIG. 3B) or sequentially at a fast rate (as represented in FIG. 3C), in order to more effectively elicit a desired evoked compound action potential, or ECAP, from the targeted tissue.

Next, a description is provided of how such an elicited ECAP is used to more effectively program, or "fit", a neurostimulator device to a patient. Typically, when a fitting system, such as the fitting system described in the previously referenced '629 or '247 patents, is employed for multichannel stimulation systems, or when equivalent or similar fitting systems are employed, it is necessary to use directly measured threshold values and/or thresholds derived from the measurement of psychophysically-determined pseudo-comfort levels. That is, for each channel of the multichannel cochlear stimulation system, a minimum threshold level is measured, typically referred to as a "T" level, which represents the minimum stimulation current which when applied to a given electrode associated with the channel produces a sensed perception of sound at least 50% of the time. In a similar manner, an "M" level is determined for each channel, which represents a stimulation current which when applied to the given electrode produces a sensed perception of sound that is moderately loud, or comfortably loud, but not so loud that the perceived sound is uncomfortable. These "T" and "M" levels are then used by the fitting software in order to properly map sensed sound to stimulation current levels that can be perceived by the patient as sound.

Disadvantageously, determining the "T" and/or "M" levels (or other required thresholds) associated with each channel of a multichannel stimulation system is an extremely painstaking and time-intensive task. Such determinations require significant time commitments on the part of the clinician, as well as the patient. Moreover, once determined one channel at a time, such levels may not be representative of actual threshold levels that are present during real speech.

Additionally, when fitting a patient with a cochlear implant, or other neurostimulation device, it is necessary and desirable to initially program the device with stimulation parameters that, when the device is first turned on, will not damage or be painful to the patient. Generally, this has required initially programming the device with very low stimulation levels, and then gradually and painstakingly increasing these levels until such time as the patient can just begin to perceive such stimulation, and going on from there. Again, such process is extremely time consuming and laborious. The techniques described in this specification advantageously shorten this process by providing a technique or tool whereby when the neurostimulation device is first implanted in the patient, and when the patient is still under the influence of an anesthesia, the surgeon and medical personnel in the operating room (OR), through use of multi-electrode stimulation to elicit an ECAP as explained above, can quickly ascertain appropriate threshold levels that can be initially programmed into the implant device for use by the device when it is first turned on. (The "turning on" of the implant device may not occur until several weeks after the surgery.) Moreover, in the process of obtaining these initial threshold levels, the proper operation of the implant device can be verified while the patient is still in the OR before the implant site is surgically closed.

Figure 4A:
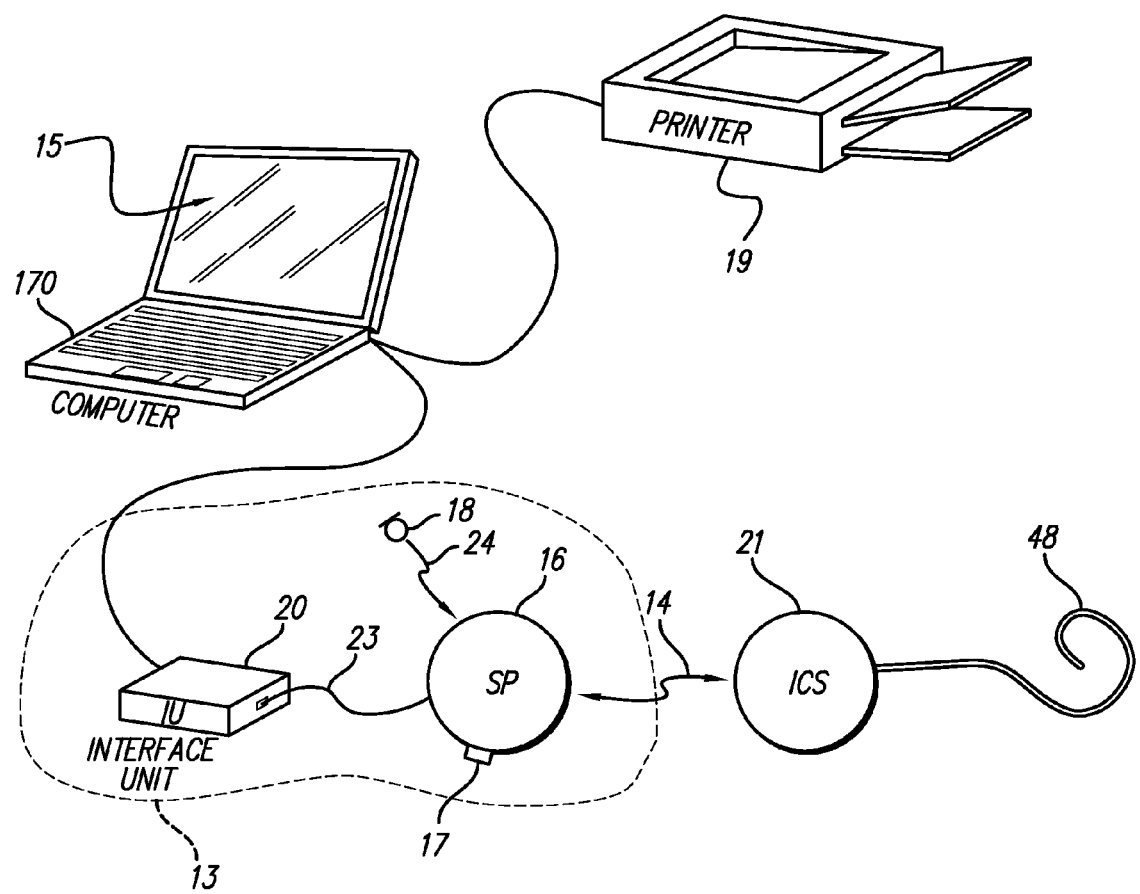
FIGS. 4A and 4B illustrate representative fitting configurations that may be used during a fitting session.
Figure 4B:
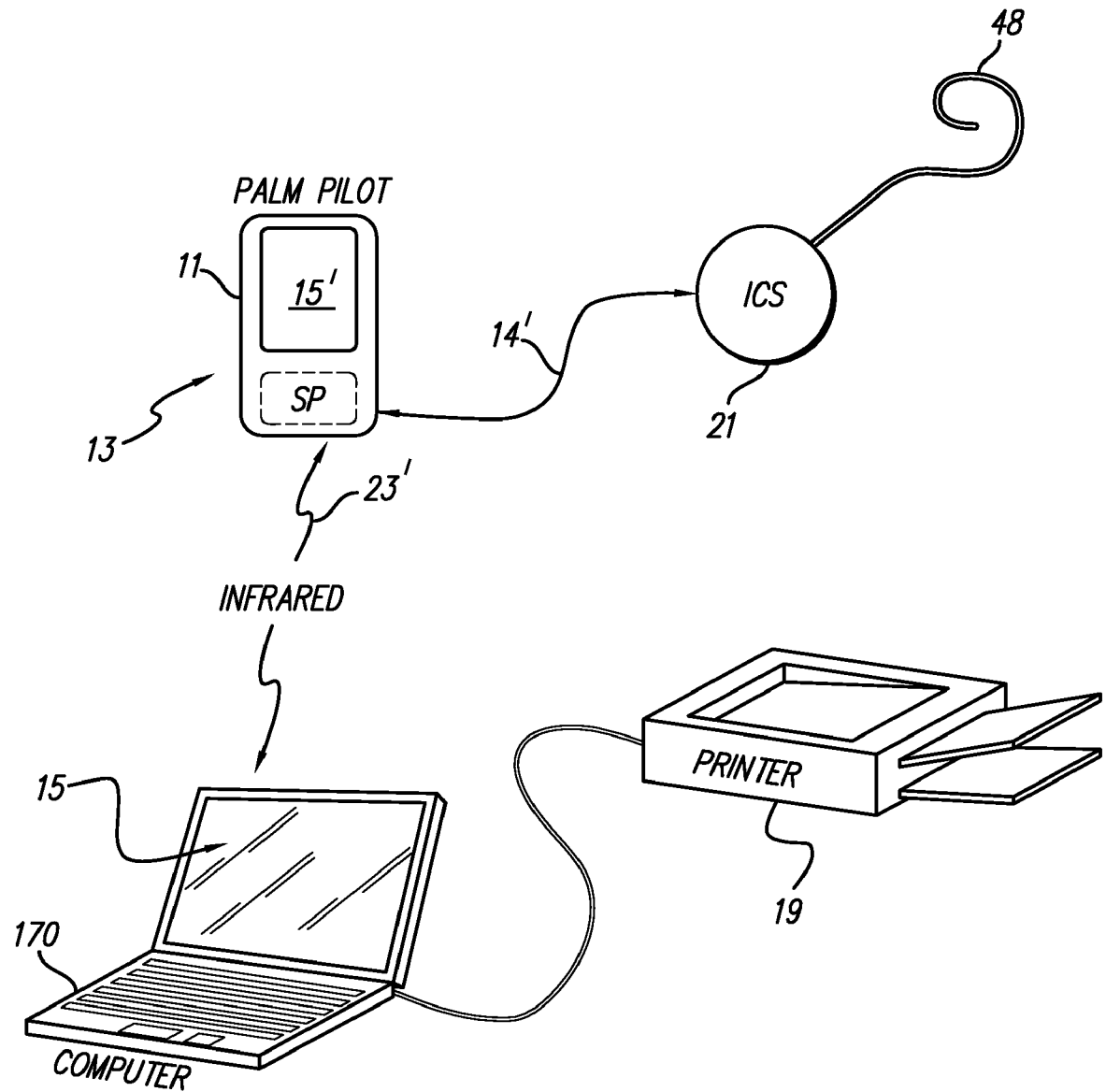

To better understand the "fitting" procedure, reference is next made to FIGS. 4A and 4B. FIG. 4A shows a block diagram of the basic components that may be used to fit a given patient with a cochlear implant system. As seen in FIG. 4A, the implant system includes the SP 16 linked to an ICS 21 with electrode array 48, the same as previously described in connection with FIG. 1. A microphone 18 is also linked to the SP 16 through a suitable communication link 24. A laptop computer 170, or other type of computer, or equivalent device, is coupled to the speech processor 16 through an interface unit (IU) 20, or equivalent device. The type of linkage 23 established between the IU 20 and the SP 16 will vary depending upon whether the SP 16 is implanted or not. Any suitable communications link 23 may be used, as is known in the art, and thus the details of the link 23 are not important for purposes of the present invention. It should be noted that for some applications, the IU 20 may be included within the computer 170 (e.g., as a communications interface already present within the computer, e.g., a serial port, or other built-in port, e.g., an IR port).

The computer 170, with or without the IU 20, provides input signals to the SP 16 that simulate acoustical signals sensed by the microphone 18, or received through the auxiliary input port 17, and/or provide command signals to the SP 16. In some instances, e.g., when testing the patient's threshold levels, the signals generated by the computer 170 replace the signals normally sensed through the microphone 18. In other instances, e.g., when testing the patient's ability to comprehend speech, the signals generated by the computer 170 provide command signals that supplement the signals sensed through the microphone 18.

The laptop computer 170 (or equivalent device) provides a display screen 15 on which selection screens, stimulation templates and other information may be displayed and defined. Such computer 170 thus provides a very simple way for the audiologist or other medical personnel, or even the patient, to easily select and/or specify a particular pattern of stimulation parameters that may be thereafter used, even if for just a short testing period, regardless of whether such stimulation pattern is simple or complex. Also shown in FIG. 4A is a printer 19 which may be connected to the computer 170, if desired, in order to allow a record of the selection criteria, stimulation templates and pattern(s) that have been selected and/or specified to be printed.

FIG. 4B illustrates an alternative fitting system that may also be used. In FIG. 4B, the ICS 21 is linked to a speech processor configured or emulated within a palm personal computer (PPC) 11, such as a Palm Pilot, or equivalent processor, commercially available, e.g., from Hewlett Packard. Such PPC 11 includes its own display screen 15' on which some graphical and textual information may be displayed. In use, the PPC 11 is linked, e.g., through an infrared link 23', to another computer, 170, as necessary. Typically, the functions of the SP and related devices are stored in a flashcard (a removable memory card that may be loaded into the PPC 11), thereby enabling the PPC 11 to perform the same functions of those elements encircled by the dotted line 13 in FIG. 4A. The PPC 11 is coupled to the ICS 21 through a suitable data/power communications link 14'.

Figure 5:
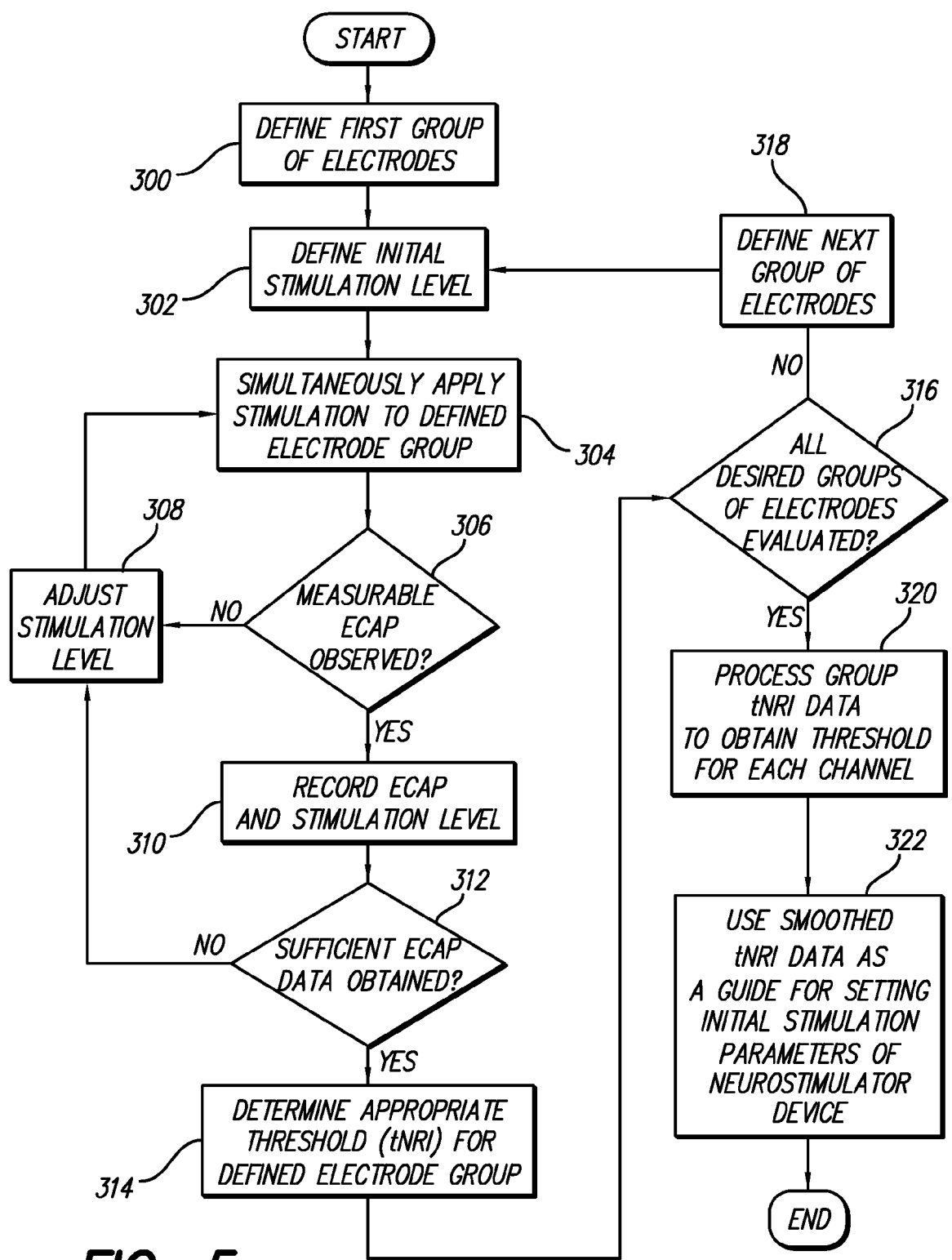
FIG. 5 is a flow chart that depicts a method of obtaining ECAP data during a fitting session.

Next, with reference to FIG. 5, a flow chart is shown that illustrates one example method of using the techniques described herein, wherein the main steps of the invention are identified in boxes or blocks that interconnect to define a flow or sequence of steps. As seen in FIG. 5, the method begins by defining a first group of electrodes that are to receive stimuli (block 300) for the purpose of eliciting an ECAP. Once such group of electrodes is defined, the next step is to define an initial intensity level for the stimuli (block 302). Once the electrode group is defined, and the intensity level of the stimuli is defined, electrical stimuli of the defined intensity (amplitude) are simultaneously applied to the defined group of electrodes (block 304). Here, it should be noted that "simultaneous" is as defined previously. Simultaneous means that the stimuli are applied at the same time to all electrodes, or that the stimuli are applied sequentially to the electrodes within the group at a sufficiently fast rate to elicit a synchronous response from the targeted tissue.

A determination is then made as to whether a measurable ECAP is elicited (block 306). To measure or observe an ECAP, it is necessary to monitor a selected "sense" electrode through a sense amplifier, or equivalent circuitry. Advantageously, the back telemetry features included in modern Cochlear implant devices, such as the CII Bionic Ear Cochlear Implant device made by Advanced Bionics Corporation, and other neurostimulator devices, allows the voltage on a given electrode contact to be monitored. Usually, such monitoring is used to measure the impedance associated with a given electrode contact, but such impedance measurement is typically made by measuring the voltage at the electrode contact and dividing the measured voltage by the current flowing through the electrode contact. Hence, the voltage at the electrode contact is one of the measured parameters that is available. Thus, the present invention monitors the selected "sense" electrode by monitoring the voltage that appears on such electrode.

If a measurable ECAP is not sensed on the contact electrode (NO branch of block 306), then the intensity of the applied stimulus is adjusted, i.e., increased, and the stimulus with the new adjusted intensity is applied again (block 304).

If a measurable ECAP is sensed on the contact electrode (YES branch of block 306), then the amplitude, e.g., the peak-to-peak amplitude, $V_{pp}$, of the measured ECAP is recorded along with the intensity level of the stimulus that elicited such ECAP (block 310).

After the ECAP data is recorded, a determination is made as to whether sufficient ECAP data has been obtained (block 312). Generally, it is desirable (as will be more apparent from the description that follows) that at least two ECAP data points, and preferably at least three or four ECAP data points, be measured and recorded.

If more ECAP data points are desired (NO branch of block 312), then the intensity level of the stimulus is adjusted to a new value (block 308), and the process of obtaining an additional ECAP data point is repeated (blocks 304, 306, 310, 312).

If sufficient ECAP data points have been determined (YES branch of block 312), then the data associated with the ECAP data points are processed to determine an appropriate neural response threshold, tNRI, for the defined electrode group (block 314). Any of several techniques may be used to determine the appropriate tNRI threshold, including graphically plotting the ECAP data points as a function of stimulus current level and extrapolating the resulting curve to a desired stimulus level, averaging the ECAP data point data, etc. One preferred technique for determining tNRI from the ECAP data for the selected electrode group is explained in more detail below in connection with the algorithm described in connection with FIGS. 6A-6G.

Once the tNRI threshold has been determined for the defined group of electrodes, a determination is made as to whether all of the desired groups of electrodes have been evaluated for determining a tNRI threshold. If not (NO branch of block 316), then a new group of electrodes is defined (block 318), and the process is repeated (blocks 302 through 316) in order to determine an appropriate tNRI threshold for the new group of electrodes.

If all of the desired groups of electrodes have been evaluated for the purpose of determining a tNRI threshold (YES branch of block 316), then appropriate processing techniques are applied to such tNRI data in order to determine an appropriate tNRI threshold for each electrode contact, i.e., for each stimulation channel (block 320). Such processing may take many forms. For example, a three-point weighted average could be used, with the first and last data points of a three-consecutive data points being weighted 25%, and the middle data point being weighted 50%. Alternatively, a b-spleen interpolation technique could be used, as could any other curve-smoothing technique known in the art.

Once the electrode group tNRI data has been smoothed (to remove discontinuities therein, e.g., at the transition from one electrode group to the next, then the resulting curve that connects the smoothed data points may be used to define the tNRI value for each electrode, or each stimulation channel. Such data may then be used to set the initial stimulation parameters (block 322), or to guide the selection of the stimulation parameters during operation of the neurostimulation device.

Those of skill in the art will recognize that the process described in the flow chart of FIG. 5 may be automated, or at least semi-automated, using a suitable external processor (such as the processor 170 (FIGS. 4A or 4B). Such processor may be programmed to implement the process using various algorithms and other programming strategies and techniques.

One preferred algorithm for carrying out the invention is represented by the series of screens shown in FIGS. 6A-6G. The screens of FIGS. 6A-6G represent various screens that may be selected for display on the display 15 of the computer 170, or other processor, as the fitting process is carried out. Such fitting process may initially be carried out in the Operating Room (OR) as the implant operation takes place. (In such case, the computer 170 may be a specially configured computer, e.g., one having a touch-sensitive screen, suitable for use in the sanitary OR environment.) When this is done, the medical personnel associated with the surgery are not only able to verify proper operation of the implant device, but they can also record and store appropriate (safe, effective and comfortable) tNRI values that may be programmed into the implant device for use when it is first turned on several weeks after the implant operation.

The algorithm may be carried out while generating input/output (I/O) data in the OR on all electrodes. More particularly, the techniques described herein include obtaining such data for groups of electrodes, e.g., four electrodes at one time, rather than obtaining data on individual electrodes. However, the group size of the number of electrodes in the group may be selected to be as small as one in the event data is desired from only a single electrode. The I/O data is obtained for a range of intensities (current stimulation pulses of different amplitudes and/or pulse widths), and is then plotted to allow tNRI data to be ascertained for each electrode.

The program described is able to save or recall and repeat measurements. Moreover, the user can pause without losing data in order to adjust parameter values, e.g., step sizes and averages. Additionally, the user can view a real-time display of the ECAP waveforms during data collection. After data collection, the user can view single traces, an I/O plot, and computed tNRI values. The user is further allowed to reject single traces. Further, the user can run the program that carries out the invention in both a manual and automated (macro) operation mode.

Figure 6A:
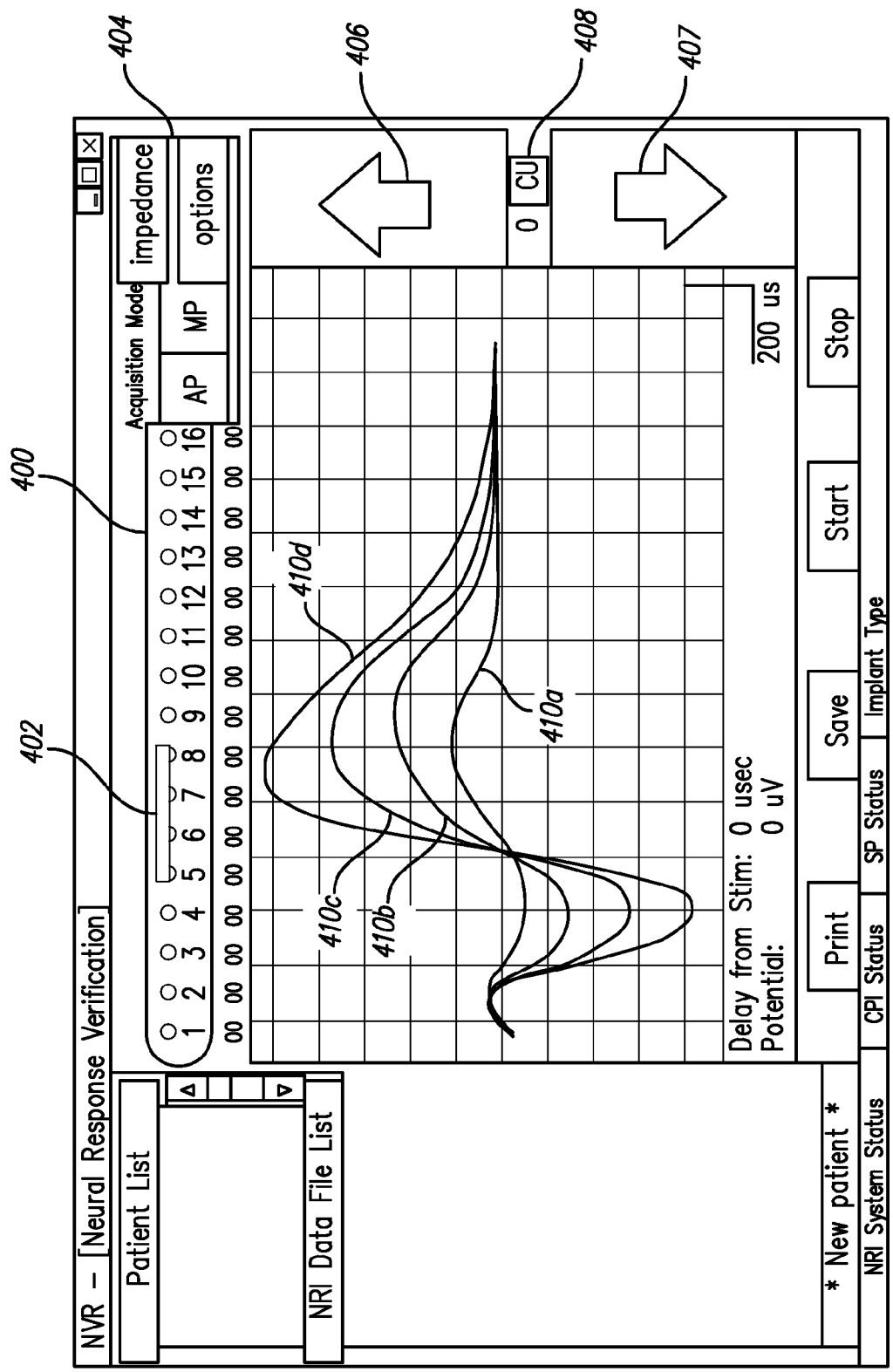

FIG. 6A shows a first screen that is generated when a manual operation mode is selected. A graphical representation 400 of the available electrodes (in this case, sixteen electrodes, E1, E2, E3, . . . E16) appears across the top of the screen. In FIG. 6A, an electrode group 402 comprising electrodes E5, E6, E7 and E8 has been selected as the electrodes that will simultaneously receive a stimulus. The main body of the screen is a grid, much like an oscilloscope screen, whereon an ECAP waveform appears when a stimulus is applied. Up and down arrows 406 and 407, respectively, on the right-hand side of the screen allow the vertical scale on the grid to be selected, or allow the amplitude of the current stimulus to be adjusted. The "CU" indication 408 means that the arrows 406 and 407 are used to control the amplitude of the "current", and that (as shown in FIG. 6A) the current is set to zero. User-selectable buttons 404 in the upper right hand corner of the screen allow the user to select "impedance" (for an impedance measurement) or "options".

By selecting a first amplitude for the stimulus current using the up arrow 406, a first ECAP waveform 410a is obtained. The amplitude of this waveform 410 a can then be measured. By increasing the amplitude of the stimulus current, a second ECAP waveform 410b is obtained. The amplitude of the ECAP waveform 410b can also be measured. Similarly, by increasing the amplitude of the stimulus current to different levels, additional ECAP waveforms 410c and 410d are obtained, each having an amplitude that can be measured. Thus, in the manner described, four ECAP data points are obtained, each point having a stimulus current amplitude and an ECAP amplitude associated therewith.

Figure 6B:
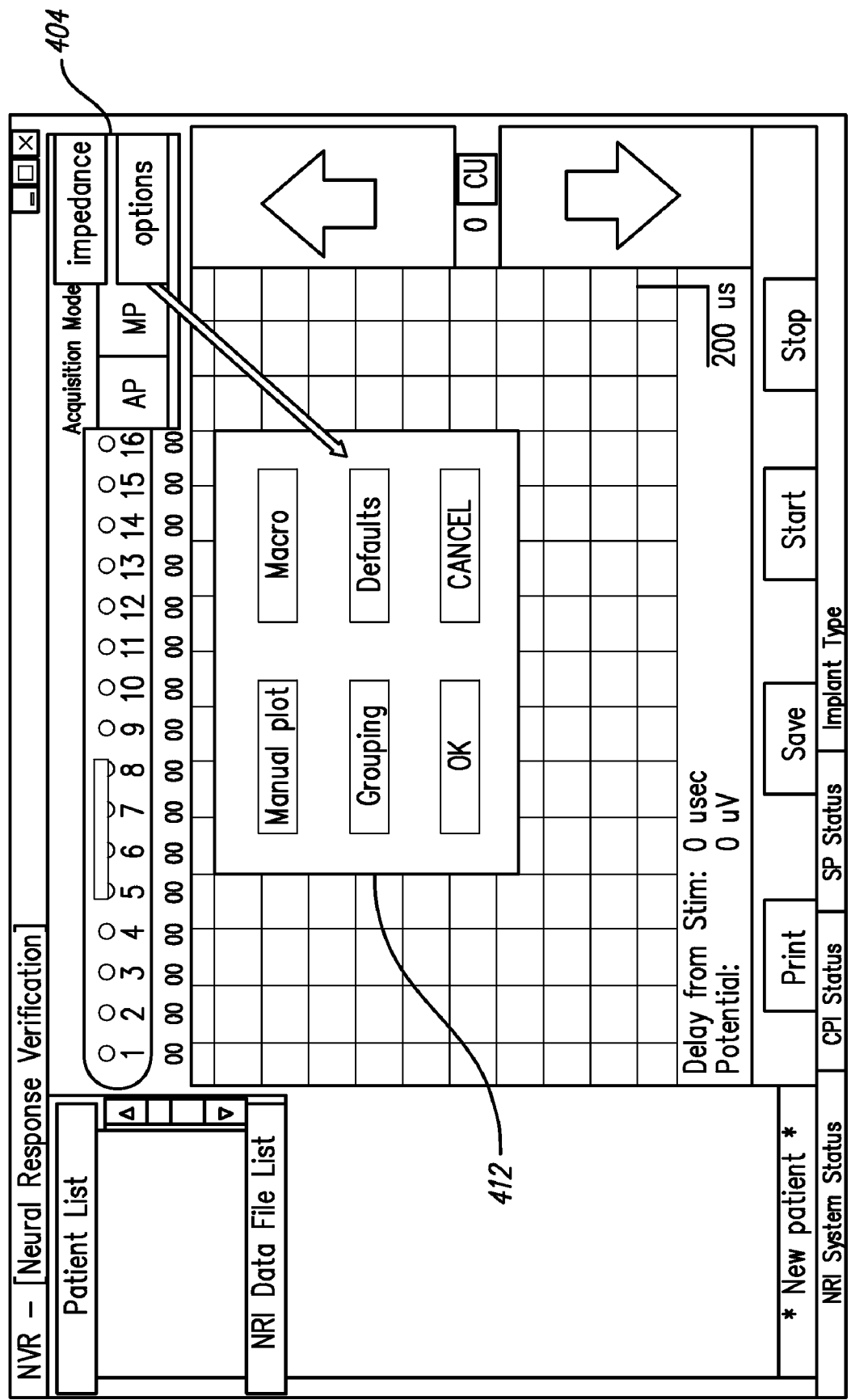
Figure 6C:
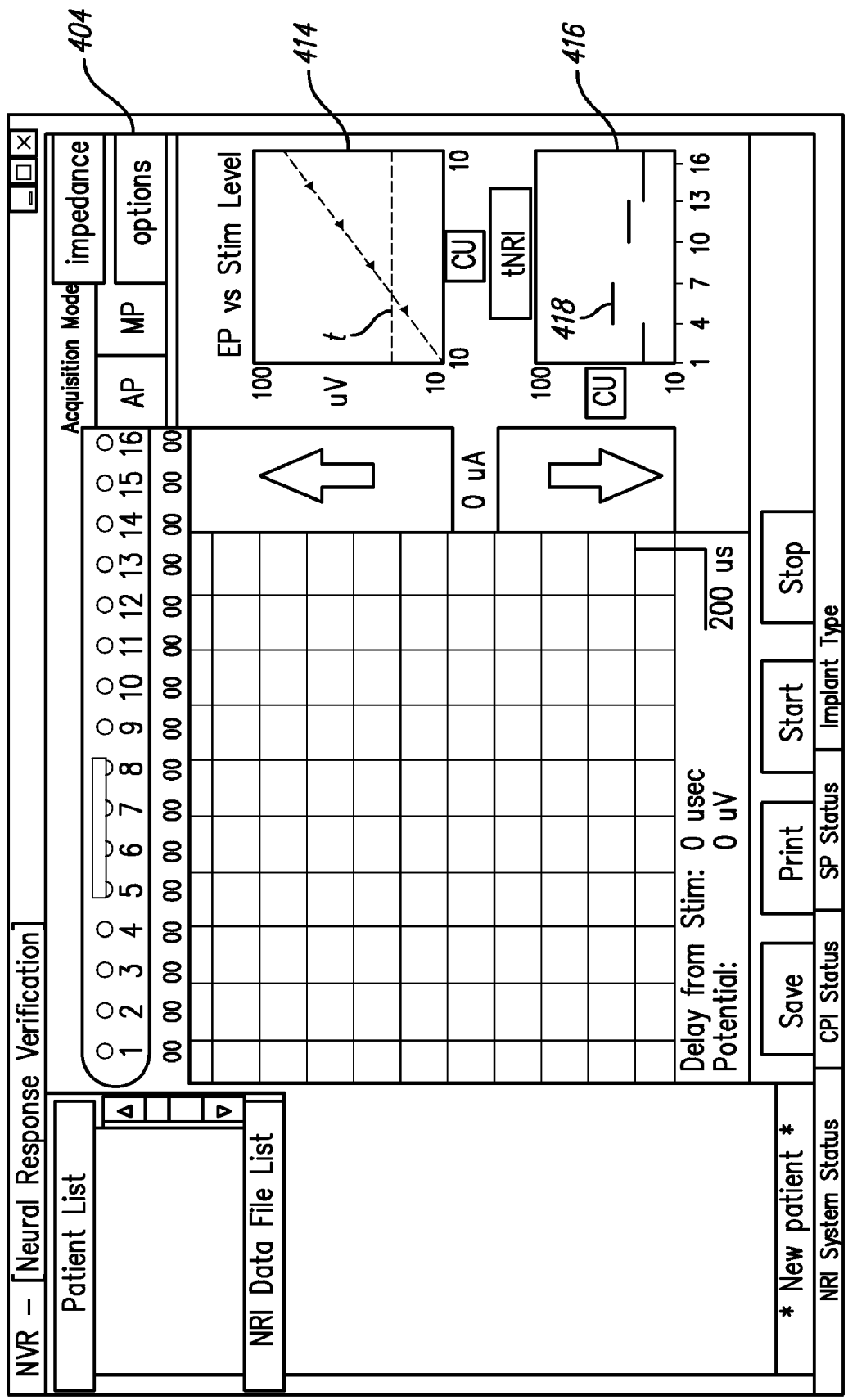

FIG. 6B illustrates what happens when the "options" button 404 is selected. As seen in FIG. 6B, such action causes another window 412 to appear in the center of the screen that contains six options that may be further selected. One of the six options that may be selected is "Manual Plot". When the "Manual Plot" option is selected, a screen as shown in FIG. 6C appears. This screen contains an "EP vs. Stim Level" area 414 whereon a plot may be made of the ECAP data points for the particular electrode group from which the ECAP data was obtained. From the plot, or from an extrapolation of the plot, a threshold line "t" may be established. Where the plot of EP vs. Stim Level crosses the "t" line becomes a threshold for that group of electrodes. This threshold, referred to as the tNRI threshold, is then plotted in a second area 416 of the screen, as segment 418. The tNRI thresholds for other electrode groupings, e.g., electrodes E1-E4, E9-E12, and E13-E16 may be similarly obtained and plotted in the tNRI plot 416.

Figure 6D:
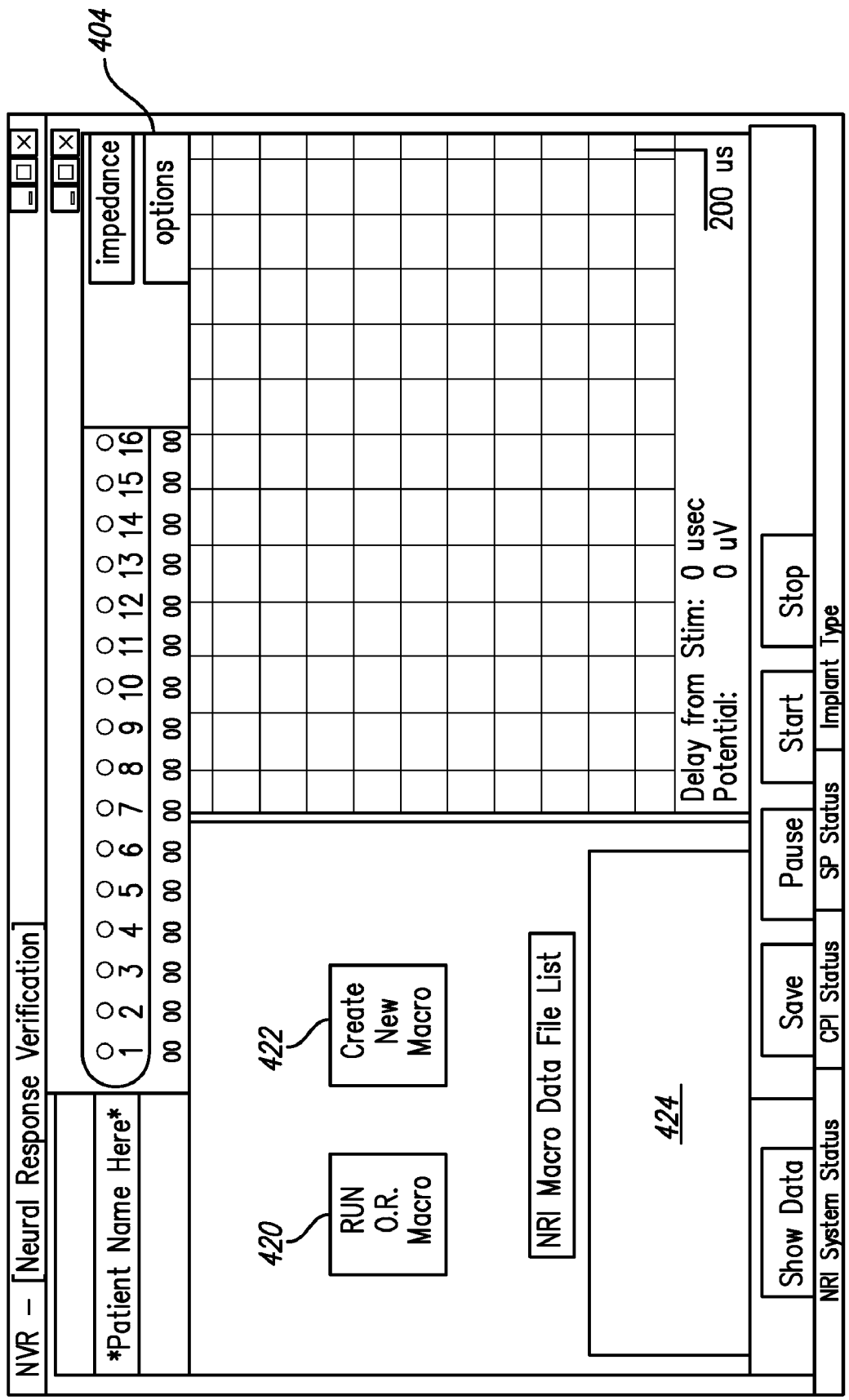

FIG. 6D shows the screen that appears when the "Macro" options is selected from the options window 412 (FIG. 6B). Selecting "Macro" allows one to run predefined values (or enter new value sets, monitor the data collection or recall previous collected data and re-run with the same stimulation parameters). For example, an OR (operating room) macro may be selected by selecting the OR macro area 420. Alternatively, a new macro may be created by selecting the "Create New Macro" area 422. Existing macros available for use are listed in the NRI Macro List window 424.

Figure 6E:
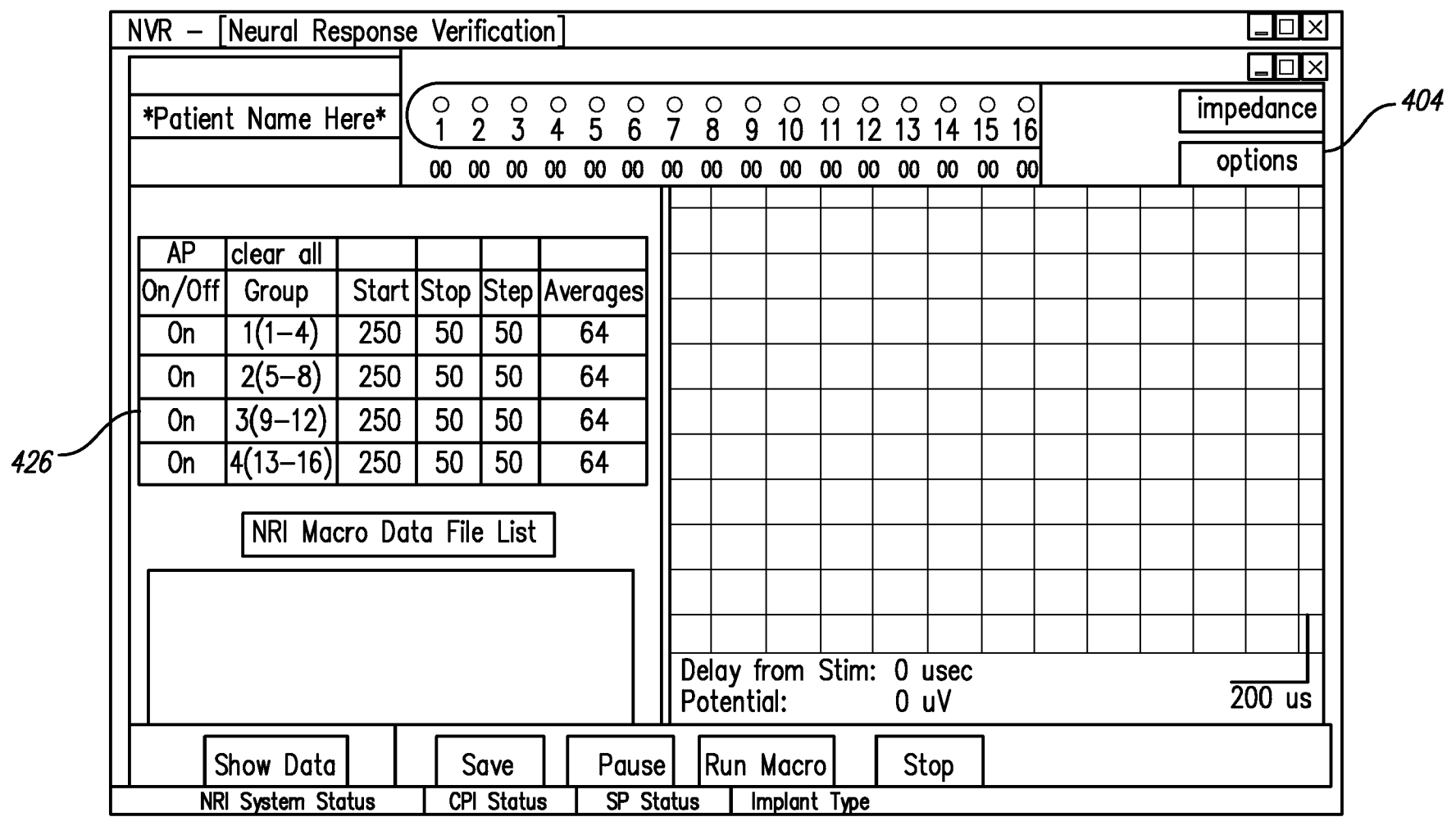

FIG. 6E illustrates the screen that appears when a "Macro" is selected to run with predefined values. The predefined values used by the macro are listed in the area 426 as a table. Start, stop, and step sizes may be defined for the current stimulus applied to each electrode group.

Figure 6F:
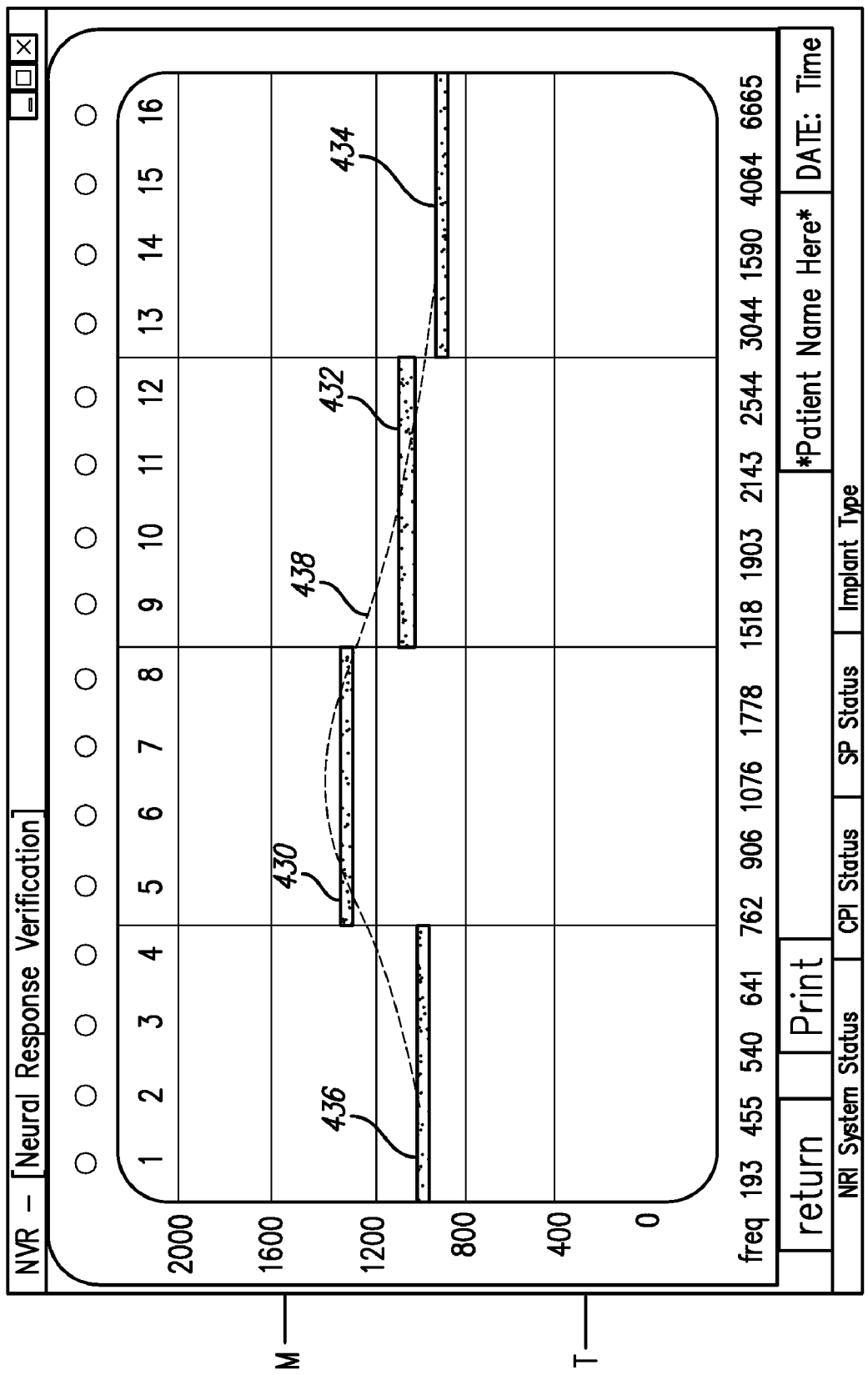

FIG. 6F illustrates the screen that is displayed when an "Analysis" option is selected from the Macro screen. This screen shows the tNRI values computed form the I/O function for each electrode group. The tNRI values for electrodes E5-E8, for example, are represented by the line segment 430. Similarly, the tNRI values for electrodes E9-E12 are represented by the line segment 432; for electrodes E13-E16, by the line segment 434; and for electrodes E1-E4, by the line segment 436. Note that all of the tNRI values shown in FIG. 6F lie between the "M" and "T" levels that would be obtained if such "M" and "T" levels were measured. One of the advantages of the invention is that the "M" and "T" levels do not need to be measured.

The tNRI values shown in FIG. 6F may be further processed to "smooth" the curve, particularly at the discontinuities at the boundaries between the electrode groups. Such further processing may take many forms. For example, a three-point weighted average could be used, with the first and last data points of three-consecutive data points being weighted 25%, and the middle data point being weighted 50%. Alternatively, a b-spleen interpolation technique could be used, as could any other curve-smoothing technique known in the art.

After smoothing, a curve, such as the curve 438 results, which curve may then be used to provide a recommended initial stimulation value for each electrode. Such recommended stimulation values will always fall within the range of "M" and "T" levels, and thus represent values that can be safe and efficacious to use as an initial stimulation value for each electrode once the implant neurostimulator device is turned on.

Figure 6G:
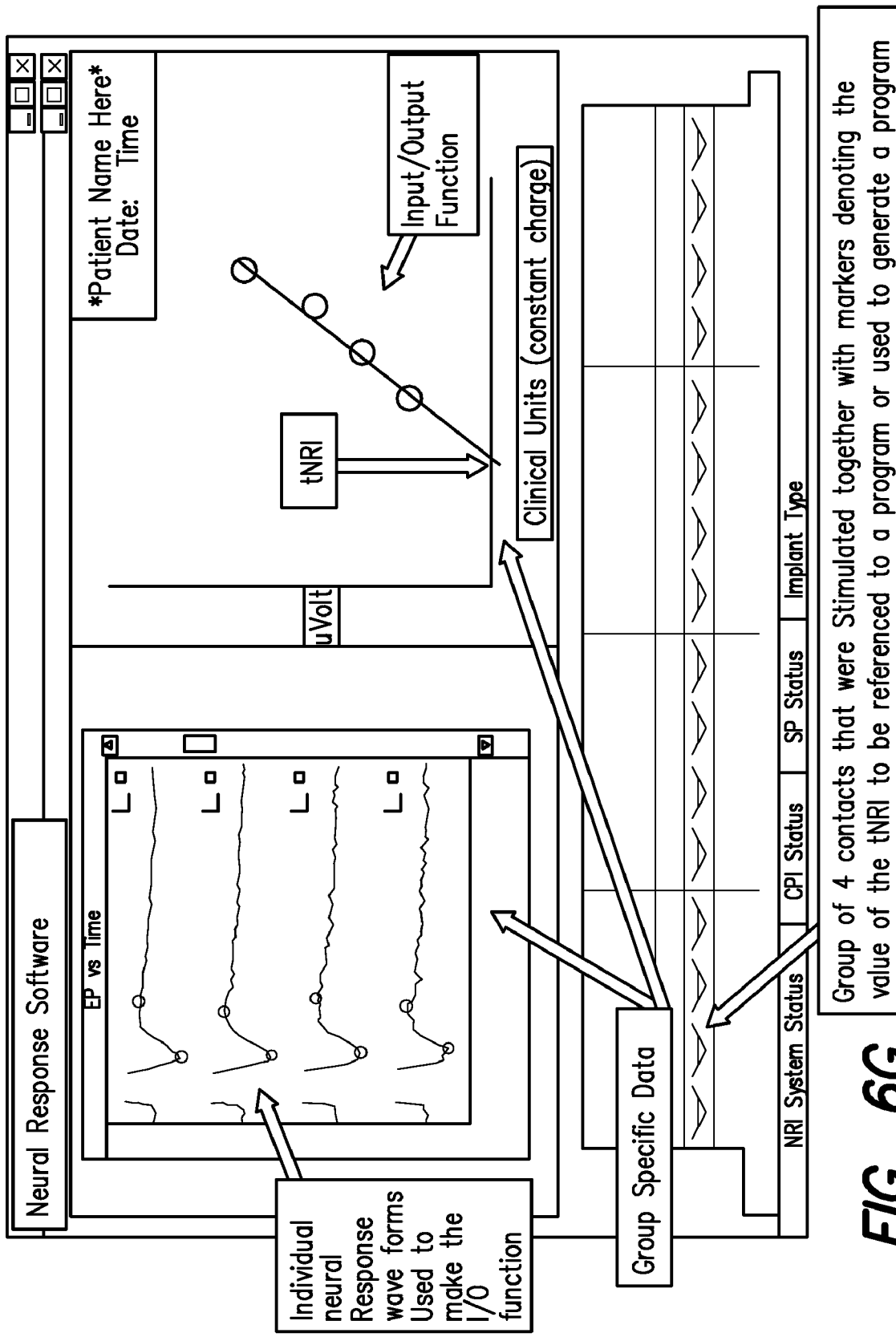

FIG. 6G shows an example of a possible display of the data collected by the algorithm of the present invention. By selecting the "group" that was stimulated together, one can see how the tNRI was computed form the input/output function, and/or the user can inspect waveforms, as well as de-select waveforms from the computation.

It is to be emphasized that using the ECAP values to determine the tNRI stimulation values as described above represents only one way in which the appropriate tNRI values can be estimated. The stapedial reflex measurements may also be used to determine appropriate stimulation levels, as described in the previously referenced co-pending patent application Ser. No. 60/412,533, filed Sep. 20, 2002. Further, the techniques taught in U.S. Pat. Nos. 5,626,629 and 6,289,247 may similarly be used.

Once an appropriate tNRI value is determined in accordance with the techniques described above, or in accordance with one of the other ways described in the referenced patents and patent applications, such value may be stored and saved for use during the initial turn-on of the implant device; or such value may be recommended for programming into a working implant device, or such value may be automatically programmed into a working implant device. One of the advantages of the present approach—of using ECAP values to determine the tNRI values—is that it can be performed quickly, and in many cases automatically. Thus, it need not be limited to use only in the OR in order to find appropriate initial tNRI values. Rather, the present approach, as well as the stapedial reflex invention described in the referenced co-pending patent application (Ser. No. 60/412,533, filed Sep. 20, 2002), can be used anytime that the implant device needs to be reprogrammed, or that stimulation levels need to be adjusted, or that the neural response derived contour needs to be shifted.

As described above, it is thus seen that the present specification provides an improved system and method of fitting a neurostimulator device by measuring the ECAP of the patient through application of multi-band (i.e., multi-electrode contact) stimulation in order to better determine appropriate intensity threshold levels used by the implant system during its operation.

It is further seen that the present specification provides such an improved system and method of fitting that does not require subjective feedback from the patient during the fitting procedure.

Moreover, it is seen that the specification provides a way to validate proper operation of the implant device at a time shortly after the device is implanted at a time when the patient may still be under the influence of an anesthesia, and hence unconscious.

While the techniques herein disclosed have been described by means of specific embodiments and applications thereof, numerous modifications and variations could be made thereto by those skilled in the art without departing from the scope of the invention set forth in the claims.

What is claimed is:

1. A cochlear implant system comprising:

multiple electrode contacts through which electrical stimuli are adapted to be applied to a patient's inner ear;

means for generating electrical stimuli with selectable degrees of amplitude intensity;

means for delivering the electrical stimuli to selected groups of electrode contacts, such that at least two of the selected groups of electrode contacts output an electrical current into the inner ear tissue;

means for gradually adjusting the intensity of the electrical stimuli to selected groups of electrode contacts;

means for detecting an occurrence of an evoked compound action potential (ECAP);

means for determining an electrical-stimuli intensity threshold level (tNRI) associated with the occurrence of the ECAP for each selected group of electrode contacts, the tNRI threshold level for all of the selected groups comprising tNRI threshold data;

means for processing the tNRI threshold data to determine a contour of tNRI threshold levels that defines a tNRI threshold for each electrode contact;

wherein the means for processing the tNRI threshold data to determine a contour of tNRI threshold levels that defines a tNRI threshold for each electrode contact comprises means for combining the tNRI threshold level data from each selected group of electrodes and means for smoothing discontinuities therein; and wherein the means for smoothing discontinuities in the tNRI threshold data comprises means for applying a three-point weighted average, with the first and last data points of a three-consecutive data points being weighted a first prescribed percentage, and with the middle data point being weighted a second prescribed percentage, where the second prescribed percentage is greater than the first prescribed percentage.

2. The system of claim 1 wherein the means for detecting the occurrence of the ECAP comprises using another separate electrode contact near the at least two of the selected groups of electrode contacts receiving the delivered electrical stimuli for the occurrence of the ECAP.

3. The system of claim 1 further comprising means for using the contour of tNRI threshold levels to define stimulation parameters thereafter used by the cochlear implant system to control the intensity of the electrical stimuli applied through the electrode contacts.

4. The system of claim 1 wherein the means for delivering the electrical stimuli to a selected group of electrode contacts comprises means for simultaneously delivering the electrical stimuli to each electrode contact within the selected group of electrode contacts.

5. The system of claim 1 wherein the means for delivering the electrical stimuli to a selected group of electrode contacts comprises means for sequentially delivering the electrical stimuli at a fast rate to the electrode contacts within the selected group of electrode contacts.

6. The system of claim 1 wherein the means for determining an electrical-stimuli intensity threshold level (tNRI) associated with the occurrence of the ECAP for each selected group of electrode contacts comprises means for measuring the magnitude of the ECAP corresponding to a plurality of electrical-stimuli intensity levels, thereby creating a data set of ECAP magnitudes with corresponding electrical-stimuli intensity levels, and means for determining from the resulting data set an appropriate threshold level.

* * * * *